United States Patent
Takimura et al.

(10) Patent No.: US 9,167,957 B2
(45) Date of Patent: Oct. 27, 2015

(54) PROBE

(75) Inventors: Toshinori Takimura, Duluth, GA (US); Soh Ohzawa, Toyonaka (JP)

(73) Assignee: Konica Minolta Advanced Layers, Inc., Tokyo (JP)

( * ) Notice: Subject to any disclaimer, the term of this patent is extended or adjusted under 35 U.S.C. 154(b) by 176 days.

(21) Appl. No.: 13/520,779

(22) PCT Filed: Jan. 7, 2011

(86) PCT No.: PCT/JP2011/050154
§ 371 (c)(1),
(2), (4) Date: Jul. 5, 2012

(87) PCT Pub. No.: WO2011/083836
PCT Pub. Date: Jul. 14, 2011

(65) Prior Publication Data
US 2012/0283576 A1    Nov. 8, 2012

(30) Foreign Application Priority Data

Jan. 8, 2010   (JP) ................................. 2010-002544
Jan. 8, 2010   (JP) ................................. 2010-002548

(51) Int. Cl.
| | |
|---|---|
| A61B 6/00 | (2006.01) |
| A61B 1/00 | (2006.01) |
| A61B 1/04 | (2006.01) |
| A61B 5/00 | (2006.01) |
| G01N 21/64 | (2006.01) |

(52) U.S. Cl.
CPC ......... *A61B 1/00167* (2013.01); *A61B 1/00096* (2013.01); *A61B 1/00188* (2013.01); *A61B 1/043* (2013.01); *A61B 5/0071* (2013.01); *A61B 5/0084* (2013.01); *G01N 21/645* (2013.01); *G01N 2021/6484* (2013.01)

(58) Field of Classification Search
CPC ............... A61B 1/00167; A61B 1/043; A61B 1/00188; A61B 1/00096; A61B 5/0071; A61B 5/0084; G01N 21/645; G01N 2021/6484
USPC .......................................................... 600/478
See application file for complete search history.

(56) References Cited

U.S. PATENT DOCUMENTS

| | | | | |
|---|---|---|---|---|
| 3,556,085 A | * | 1/1971 | Takahashi | 600/129 |
| 4,718,417 A | * | 1/1988 | Kittrell et al. | 606/7 |
| 4,815,816 A | * | 3/1989 | Schneider | 385/116 |

(Continued)

FOREIGN PATENT DOCUMENTS

| | | |
|---|---|---|
| JP | 10225438 | 8/1998 |
| JP | 2002301018 | 10/2002 |

(Continued)

*Primary Examiner* — Bo J Peng
(74) *Attorney, Agent, or Firm* — Cozen O'Connor (57) ABSTRACT

A probe which is inserted into a lumen of inside of a body, irradiates an observation object part of a physiological tissue with excitation light, and detects fluorescence resulting from the excitation light, wherein the probe including: a plus lens arranged facing toward a tip side of the probe; and a plurality of optical fibers receiving the fluorescence at tip surfaces through the plus lens, wherein the tip surface are directed toward the plus lens and arranged in positions offset from an optical axis of the plus lens, wherein positions of the tip surface of at least optical fibers of which an amount of offset from the optical axis of the plus lens differ mutually among plurality of optical fibers are shifted mutually along the optical axis of the plus lens.

4 Claims, 5 Drawing Sheets

(56) References Cited

U.S. PATENT DOCUMENTS

| | | | |
|---|---|---|---|
| 5,197,470 A * | 3/1993 | Helfer et al. | 600/342 |
| 5,773,835 A | 6/1998 | Sinofsky | |
| 6,011,889 A * | 1/2000 | Daniel et al. | 385/117 |
| 6,577,391 B1 | 6/2003 | Faupel et al. | |
| 6,870,620 B2 | 3/2005 | Faupel et al. | |
| 2005/0192480 A1 * | 9/2005 | Toriya et al. | 600/182 |
| 2008/0243031 A1 * | 10/2008 | Seibel et al. | 600/566 |
| 2009/0002794 A1 | 1/2009 | Weir | |

FOREIGN PATENT DOCUMENTS

| | | |
|---|---|---|
| JP | 2005237436 | 9/2005 |
| JP | 2006317319 | 11/2006 |

* cited by examiner

PROBE

RELATED APPLICATIONS

This is a U.S. national stage of application No. PCT/JP2011/050154, filed on Jan. 7, 2011. Priority is claimed on the following applications: Japan Application No.: 2010-002548 filed on Jan. 8, 2010 and Japan, Application No.: 2010-002544 filed on Jan. 8, 2010, the disclosure contents of both of which are hereby incorporated herein by reference.

FIELD OF THE INVENTION

The present invention relates to an optical probe.

DESCRIPTION OF RELATED ART

Conventionally, the probe which irradiates with excitation light to the observation object part of a physiological tissue, and detects fluorescence generated from the drag beforehand injected into living body and a physiological tissue by this excitation light is developed, and the probe is used for diagnosis of disease state (for example, the kind of a disease and infiltration range) such as the degeneration of a physiological tissue, and the cancer (for example, refer to Patent Literature 1-3).

A tip face of the optical fiber for performing the irradiation of the excitation light and the reception of the fluorescence is arranged at a tip part of the optical probe towards the tip side.

EARLIER TECHNOLOGICAL LITERATURE

Patent Literature

Patent Literature 1: U.S. Pat. No. 6,577,391
Patent Literature 2: U.S. Pat. No. 6,870,620
Patent Literature 3: Japanese Unexamined Patent Application Publication No 2002-301018

SUMMARY OF THE INVENTION

Problems to be Solved by the Invention

However, since the conventional optical probe receives only fluorescence which enters from a front direction of the optical probe when a conventional optical probe is inserted into the lumen such as esophagus, receiving the fluorescence from the surface of a wall located in the side is hard, and a precision of diagnosis will fall.

The problem of the present invention is to provide the probe for receiving certainly the fluorescence from the surface of the wall located in the side.

Means for Solving the Problems

The invention described in Claim 1 is characterized by a probe which is inserted into a lumen of inside of a body, irradiates an observation object part of a physiological tissue with excitation light, and detects fluorescence resulting from the excitation light, wherein the probe including: a plus lens arranged facing toward a tip side of the probe; and a plurality of optical fibers receiving the fluorescence at tip surfaces through the plus lens, wherein the tip surface are directed toward the plus lens and arranged in positions offset from an optical axis of the plus lens, wherein positions of the tip surface of at least optical fibers of which an amount of offset from the optical axis of the plus lens differ mutually among plurality of optical fibers are shifted mutually along the optical axis of the plus lens.

The invention described in Claim 2 is characterized by the probe described in claim 1, wherein when the tip surfaces of the plurality of optical fibers are arranged closer the tip side of the probe, the tip surfaces are closer to the optical axis of the plus lens.

The invention described in Claim 3 is characterized by any one of the probe described in claim 1 or 2, wherein the tip surfaces of the plurality of optical fibers are arranged in a shape of a concentric circular about the optical axis of the plus lens.

The invention described in Claim 4 is characterized by any one of the probe described in any one of claims 1 to 3, further includes a moving mechanism section moving at least one of the plus lens and the plurality of optical fibers along optical axis of the plus lens.

The invention described in Claim 5 is characterized by a probe which is inserted into a lumen of inside of a body, irradiates an observation object part of a physiological tissue by excitation light, and detects fluorescence resulting from the excitation light, wherein the probe including: an objective optical system having at least two lenses opposed mutually which are arranged and directed toward a tip side of the probe; a plurality of optical fibers receiving the fluorescence at tip surfaces through the objective optical system, wherein the tip surfaces are directed toward the objective optical system and arranged in positions offset from an optical axis of the objective optical system; and a moving mechanism section moving at least two of the said two lenses at the objective optical system and the plurality of optical fibers along optical axis of the objective optical system.

The invention described in Claim 6 is characterized by the probe described in claim 5, wherein positions of the tip surface of optical fibers that an amount of offset from optical axis of the objective optical system differ mutually at least among a plurality of optical fiber is shifted mutually along optical axis of the objective optical system.

The invention described in Claim 7 is characterized by any one of the probe described in any one of claims 5 to 6, wherein when the tip surfaces of a plurality of optical fibers are arranged closer the tip side of the probe, the tip surfaces are closer to optical axis of the objective optical system.

The invention described in Claim 8 is characterized by the probe described in any one of claims 6 to 7, wherein the tip surfaces of the plurality of optical fibers are arranged in a shape of a concentric circular about the optical axis of the objective optical system.

The invention described in Claim 9 is characterized by any one of the probe described in any one of claims 1 to 8, further includes a balloon inflating in a diameter direction of the probe at a peripheral part to be stuck to the inner wall of lumen.

Advantages of the Invention

Since the invention of the claim 1 is applied a plus lens arranged facing toward a tip side of the probe, a plurality of optical fibers receiving the fluorescence at tip surfaces through the plus lens, a plurality of optical fibers are arranged in positions wherein the tip surface are directed toward the plus lens and arranged in positions offset from an optical axis of the plus lens, when the probe is inserted into a lumen such as an esophagus, the fluorescence from the wall surface located in the side of the probe is converged (image formation) to the tip side of each optical fiber. And since the positions of the tip surface of at least a plurality of optical fibers of which an amount of offset from the optical axis of the plus lens differ mutually among plurality of optical fibers are shifted mutually along the optical axis of the plus lens, the fluorescence from the wall surface of the probe side in each different position along the optical axis of the plus lens is converged (image formation) to the tip surface of each optical fiber. Therefore, the fluorescence from the wall surface of the side of the probe is certainly receivable.

Moreover, since a plurality of optical fibers for receiving light is provided, the fluorescence from a plurality of an observation object part is detectable, respectively. Therefore, diagnostic speed is accelerable.

According to the invention of the claim 2, when the tip surfaces of the plurality of optical fibers are arranged closer the tip side of the probe, the tip surfaces are closer to the optical axis of the plus lens, the fluorescence from the wall surface of the probe side in each different position along the optical axis of the plus lens is certainly converged (image formation) to the tip surfaces of each optical fiber. Therefore, the fluorescence from the surface of a wall located in the probe side is certainly receivable.

According to the invention of the claim 3, since the tip surfaces of the plurality of optical fibers are arranged in a shape of a concentric circular about the optical axis of the plus lens, the fluorescence is detectable from the annular observation object part.

According to the invention of the claim 4, since at least one of the plus lens and the plurality of optical fibers is moved along optical axis of the plus lens, the position of the observation object part and the degree of converging (image formation) can be changed.

Since the invention of the claim 5 is provided with an objective optical system having at least two lenses opposed mutually which are arranged and directed toward a tip side of the probe, a plurality of optical fibers receiving the fluorescence at tip surfaces through the objective optical system, wherein the tip surfaces are directed toward the objective optical system and arranged in positions offset from an optical axis of the objective optical system, and a moving mechanism section moving at least two of the said two lenses at the objective optical system and the optical fibers along optical axis of the objective optical system, so the probe changes the degree of converging (image formation) and focal length of the objective optical system, and converges the fluorescence from the wall surface of a different distance of the probe side to the tip surface of each optical fiber. Therefore, when the probe is inserted in lumen such as esophagus, the fluorescence from the wall surface located in the side of the probe is received.

Since a plurality of optical fibers are provided, fluorescence from a plurality of the observation object part is detectable, respectively. Therefore, diagnostic velocity is accelerable.

According to the invention of the claim 6, since the position of the tip surface of optical fibers that an amount of offset from optical axis of the objective optical system differ mutually at least among a plurality of optical fiber is shifted mutually along optical axis of the objective optical system, the fluorescence from the wall surface of the probe side in each different position along the optical axis of the objective optical system is converged (image formation) to the tip surface of each optical fiber. Therefore, the fluorescence from the wall surface of the side of the probe is certainly receivable.

According to the invention of the claim 7, when the tip surfaces of a plurality of optical fibers are arranged closer the tip side of the probe, the tip surfaces are closer to optical axis of the objective optical system, the fluorescence from the wall surface of the probe side in each different position along the optical axis of the objective optical system is certainly converged (image formation) to the tip surface of each optical fiber by the objective optical system. Therefore, the fluorescence from the surface of a wall located in the probe side is more certainly receivable.

According to the invention of the claim 8, the tip surfaces of the plurality of optical fibers are arranged in the shape of a concentric circular about the optical axis of the objective optical system, the fluorescence is detectable from the annular observation object part.

According to the invention of the claim 9, the probe is provided a balloon inflating in a diameter direction of the probe at a peripheral part to be stuck to the inner wall of lumen, so the observation object part can be prevented from shifting during observation.

DETAILED DESCRIPTION OF THE PREFERRED EMBODIMENTS

Hereafter, the embodiment of the present invention is explained with reference to figures.

Figure 1:
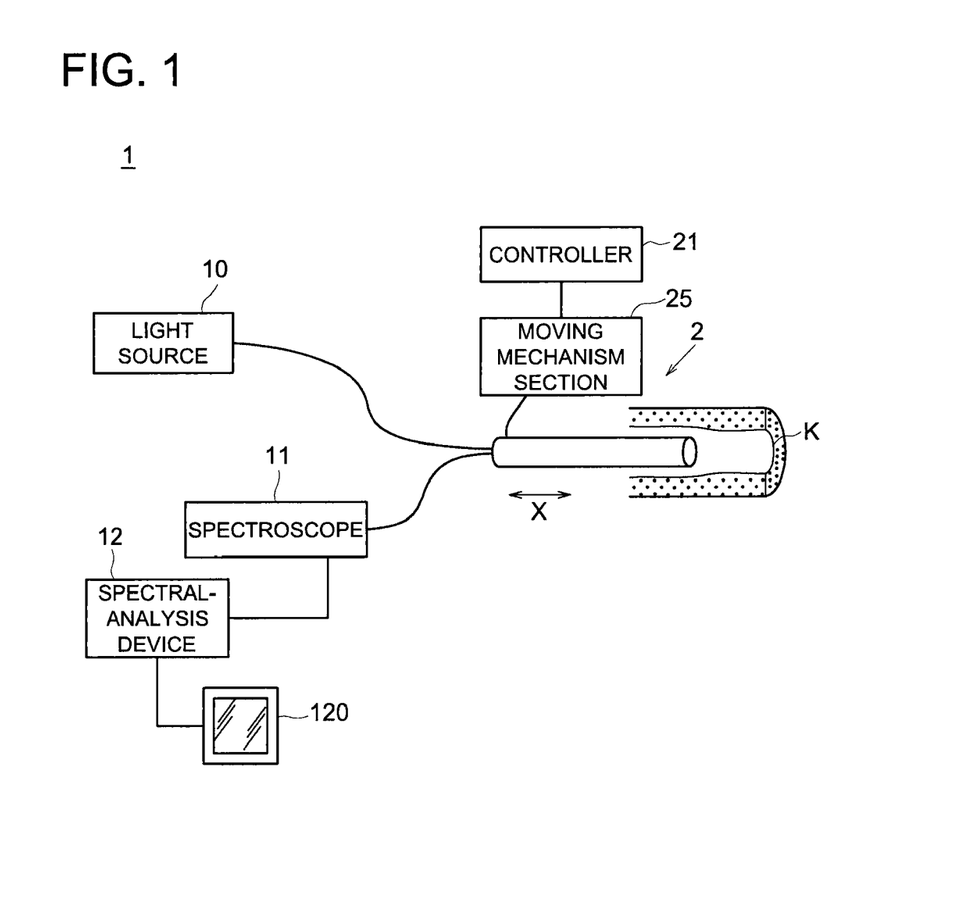
FIG. 1 is a conceptual view showing an entire constitution of a diagnostic apparatus.

FIG. 1 is a conceptual view showing an entire constitution of a diagnostic apparatus 1 which adopted the optical probe.

As shown in this figure, diagnostic apparatus 1 is apparatus which diagnoses the disease state (for example, the kind of a disease and infiltration range) such as the degeneration of a physiological tissue, and the cancer in lumen K in the living body, and has light source 10, optical probe 2, spectroscope 11 and spectral-analysis device 12.

The light source 10 generates excitation light such as xenon light, and is connected with the optical probe 2 through the wavelength selection filter.

Figure 2A:
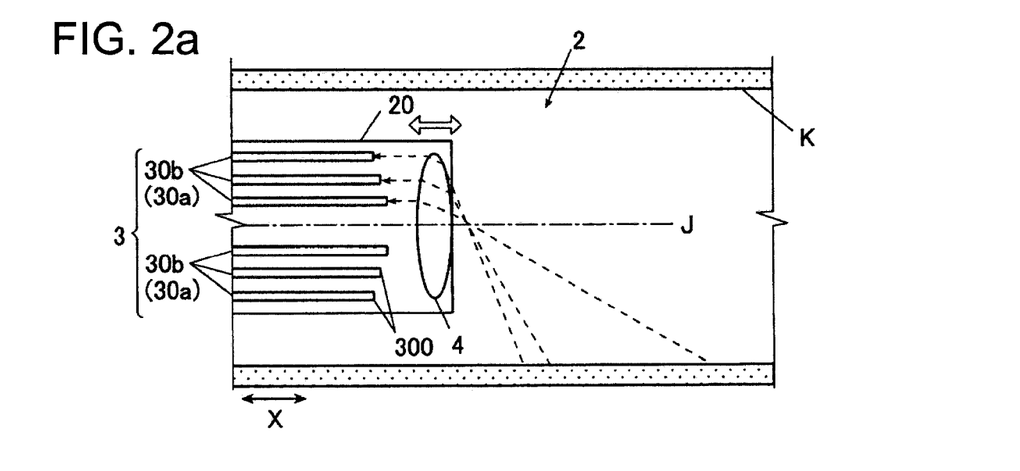
FIG. 2 is a conceptual view showing a schematic constitution of an optical probe in the first embodiment.

The optical probe 2 is inserted in lumen K in the living body along the direction of an axis X, and has the objective optical system 4 and optical fiber group 3 in the tubular sheath 20 as shown in FIG. 2a.

[Probe 2 Concerning the 1st Embodiment]

The objective optical system 4 in the embodiment shown in FIG. 2 and below-mentioned FIG. 3 consists of plus lenses (converging lens) which has plus refractive power. The plus lens is sufficient whether constituted with a single lens or a lens system constituted with two or more lenses. This objective optical system 4 is arranged towards the tip side of the optical probe 2, and coincides the optical axis J of the objective optical system 4 (plus lens) with the central axis of the optical probe 2 in the present embodiment. In addition, as such an objective optical system 4, a well known lens system from the former can be used.

The optical fiber group 3 irradiates with excitation light generated by light source 10 to the observation object part of a physiological tissue, and receives the fluorescence which originated in this excitation light and is emitted from a physiological tissue or a drag beforehand injected into living body. This optical fiber group 3 has a plurality of optical fiber 30b for receiving the fluorescence.

These plural optical fiber 30b are directed toward the tip surface 300 to the objective optical system 4, are arranged by the position offset from the optical axis J of the objective optical system 4, and receives the fluorescence passing the objective optical system 4 from the tip surface 300. A plurality of the tip surface 300 is arranged in the shape of a concentric circular about the optical axis J of the objective optical system 4, the mutual position of the tip surface 300 is shifted along the optical axis J (the direction of an axis X of the optical probe 2) of the objective optical system 4 according to the amount of offset from the optical axis J of the objective optical system 4, and in the present embodiment, when the tip surface 300 is arranged closer the tip side of the optical probe 2, the tip surface 300 is close to the optical axis J of the objective optical system 4, that is the amount of offset is small. However, the tip surface 300 is arranged by the other embodiment as long as the position of the tip surface 300 of the optical fiber 30b of which amounts of offset from the optical axis J of the objective optical system 4 differ mutually at least among the plurality of optical fiber 30b.

Figure 2B:
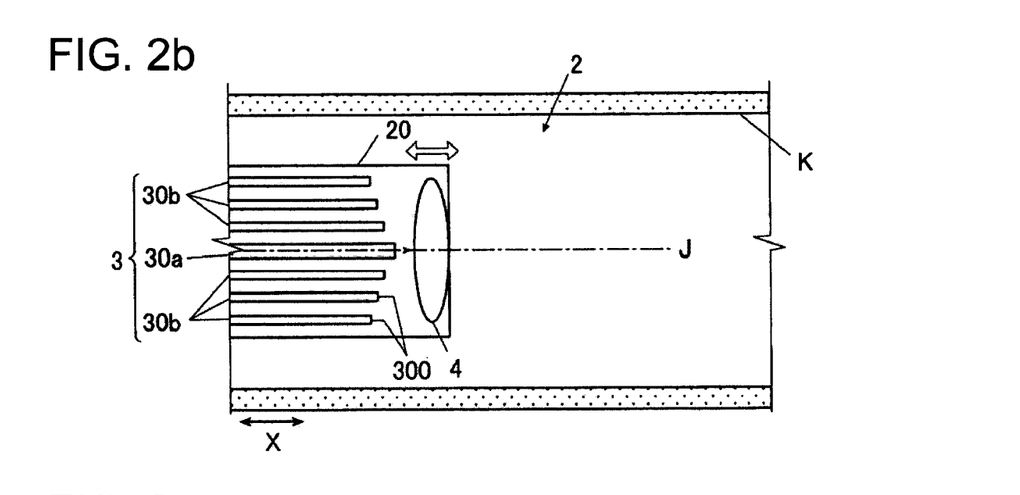
Figure 2C:
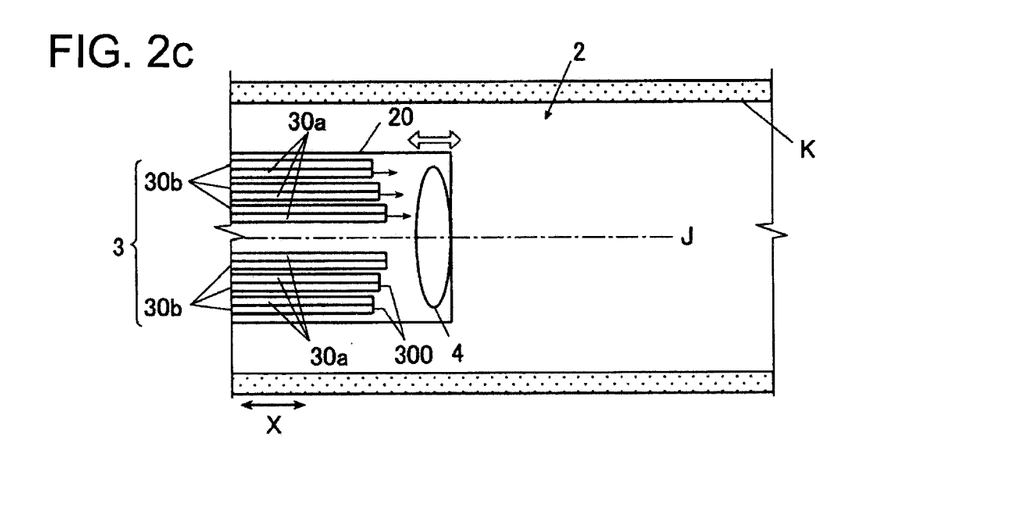

The optical fiber group 3 has optical fibers 30a for irradiating the excitation light which is generated by the light source 10 and irradiated as an emission light, parallel light or convergence light to the observation object part of physiological tissue through the objective optical system 4. This optical fiber 30a is sufficient the same as that of optical fiber 30b for receiving light as shown in FIG. 2a, it is sufficient the separate as shown in FIGS. 2b and 2c. In addition, in FIG. 2b, the only one optical fiber 30a is formed on the optical axis J of the objective optical system 4, and a plurality of optical fiber 30a is arranged side by side to each optical fiber 30b in FIG. 2c. However, the optical fiber 30a of FIG. 2c irradiates an excitation light (convergence light) which amount of the diffusion degree is small only to the observation object part through the objective optical system 4, in contrast, the optical fiber 30a of FIG. 2b irradiates the excitation light (emission light) which amount of the diffusion degree is larger than the optical fiber 30a of FIG. 2c through the objective optical system 4, since it is necessary to irradiate the excitation light with the observation object part corresponding to each optical fiber 30b.

In addition, as for the above optical fiber 30a and 30b are desirable to consist of bundle fibers.

Moreover, the optical probe 2 is provided with the moving mechanism section 25 which moves at least one of the objective optical system 4 (plus lens) and optical fiber group 3 along the optical axis J of the objective optical system 4, this moving mechanism section 25 is connected with controller 21 for an operator to operate. This moving mechanism section 25 optimizes the intensity of the fluorescence received by the optical fiber 30b (convergence degree by the objective optical system 4) and the position of the observation object part by moving the objective optical system 4 or the optical fiber group 3. In addition, FIG. 2 and below-mentioned FIG. 3 are illustrating situation that the objective optical system 4 among the objective optical system 4 and optical fiber group 3 moves by the moving mechanism section 25 (refer to the arrow in a figure). Moreover, the objective optical system 4 is desirable to move in the sealed space in the optical probe 2. Moreover, as the above moving mechanism section 25, well-known mechanisms, such as a cam mechanism or voice coil motor, is applied, for example.

A spectroscope 11 measures intensity of some wavelength from the detected fluorescence by optical fiber 30 for receiving light which is provided in the optical probe 2 (henceforth "spectrometry"), outputs the measurement result as electronic information (spectroscopic spectrum signal).

A spectral-analysis device 12 analyses the optical spectrum signal outputted by the spectroscope 11, converts the optical spectrum signal into image data of a spectroscopic spectrum graph, diagnoses disease state. Moreover, an image data and a diagnostic result of the spectroscopic spectrum graph which are generated by the spectral-analysis device 12 are displayed on to monitor 120.

In addition, well known things is applied for example, such as a disclosed thing of Japanese Unexamined Patent Application Publication No. H7-155286, Japanese Unexamined Patent Application Publication No. H7-204156, Japanese Unexamined Patent Application Publication No. H10-239517, Japanese Unexamined Patent Application Publication No. H10-295632, Japanese Unexamined Patent Application Publication No. H11-223726, Japanese Unexamined Patent Application Publication No.2005-319212, as light source 10, spectroscope 11, and Spectral-analysis device 12.

Since the optical probe 2 of diagnostic apparatus 1 is applied the objective optical system 4 arranged towards the tip side of the optical probe 2 and a plurality of optical fiber 30b to receive fluorescence from the tip surface 300 through the objective optical system 4, a plurality of optical fiber 30b is arranged by the position which directed toward the tip surface 300 to the objective optical system 4, and is offset from the optical axis J of the objective optical system 4, as a dashed line shows in FIG. 2a, when the optical probe 2 is inserted in lumen K such as an esophagus, the fluorescence from the wall surface located in the side of the optical probe 2 is converged to the tip surface 300 of each optical fiber 30b. And since the position of the tip surface 300 of the optical fiber 30b where the amounts of offset from the optical axis J of the objective optical system 4 differ mutually at least among a plurality of optical fiber is mutually shifted along the optical axis J of the objective optical system 4, the fluorescence from the wall surface of the probe side in each different position along the optical axis J of the objective optical system 4 is converged (image formation) to the tip surface 300 of each optical fiber 30b. Therefore, the fluorescence from the wall surface of the side of the optical probe is certainly receivable. Moreover, fluorescence can be detected from plural part, without moving the main part portion of the optical probe 2 in the direction of optical axis J of the objective optical system 4.

Moreover, since the tip surface 300 of a plurality of optical fiber 30b for receiving light is provided, the fluorescence from a plurality of a observation object part is detectable, respectively. Therefore, diagnostic speed is accelerable.

Moreover, when the tip surface 300 of a plurality of optical fiber 30b for receiving light is arranged closer the tip side of the optical probe 2, the tip surface 300 is close to the optical axis J of the objective optical system 4, the fluorescence from the wall surface of the probe side in each different position along the optical axis J of the objective optical system 4 is certainly converged (image formation) to the tip surface 300 of each optical fiber 30b. Therefore, the fluorescence from the surface of a wall located in the probe side is certainly receivable.

Moreover, since the tip surface 300 of a plurality of optical fibers 30b is arranged in the shape of a concentric circular about the optical axis J of the objective optical system 4, the fluorescence is detectable from the annular observation object part.

Moreover, at least one of the objective optical system 4 and a plurality of optical fiber 30b moves along the optical axis J of objective optical system 4, the position of the observation object part and the degree of converging (image formation) can be changed.

In addition, an embodiment which can apply the present invention can be suitably changed in the range which does not deviate from the meaning of the present invention, without being limited to the above-mentioned embodiment.

For example, although the optical probe 2 is explained as providing the moving mechanism section 25, it is good also as not providing. In this case, it is desirable that the tip surface 300 of the optical fiber 30*b* is arranged at an image formation position of the fluorescence by a plus lens beforehand.

Figure 3A:
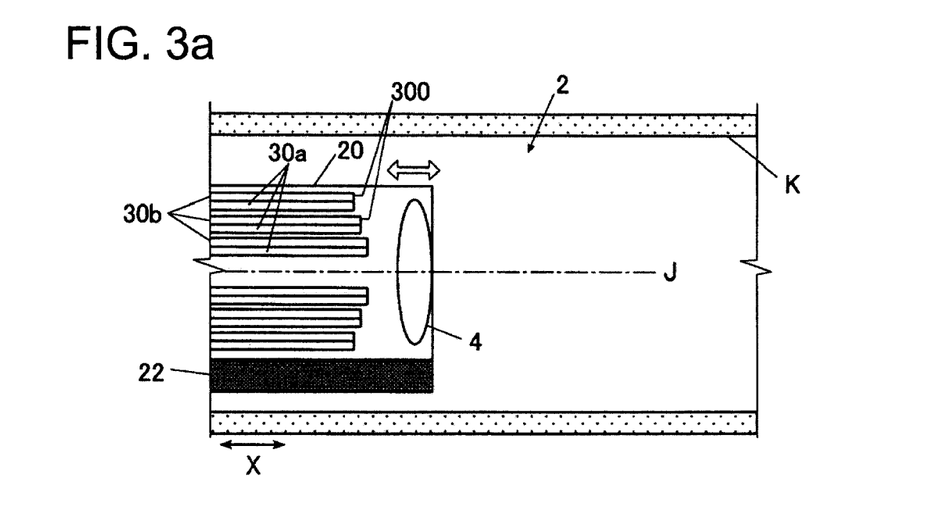
FIG. 3 is a conceptual view showing a schematic constitution of an optical probe in the first embodiment.

Moreover, as shown in FIG. 3*a*, it is desirable that the optical probe 2 is equipped a camera 22 which takes a photograph along the direction of an axis X. In this case, the state in lumen K can be sighted.

Figure 3B:
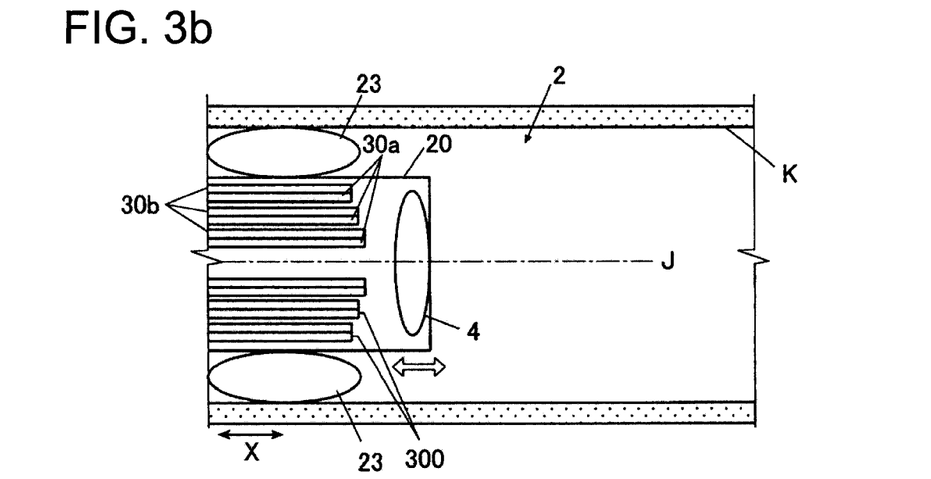

Moreover, as shown in FIG. 3*b*, it is desirable that the optical probe 2 is equipped a balloon 23 which inflates in the diameter direction (the rectangular direction to the direction of an axis X) and sticks to the inner wall of lumen K. In this case, the observation object part can be prevented from shifting during observation.

[Probe 2 Concerning the 2nd Embodiment]

In 1st embodiment, the fluorescence from the wall surface of side of the optical probe in each different position along the optical axis J is made to converge (image formation) to the tip surface of each optical fiber, and certainly receiving the fluorescence from the wall surface of side of the optical probe, when an objective optical system 4 which provided with single plus lens is used, and the tip surface 300 of the plurality of optical fiber which the amount of offset from the optical axis J is differ mutually has composition from which the position of the tip surface 300 is mutually shifted along the optical axis J. In 2nd embodiment, the same effect as the 1st embodiment is acquired when an objective optical system 4 which provided with at least two plus lenses are used, and the moving mechanism section which moves at least one of the optical fiber and the two plus lenses along the optical axis J is provided. It explains below.

Figure 4A:
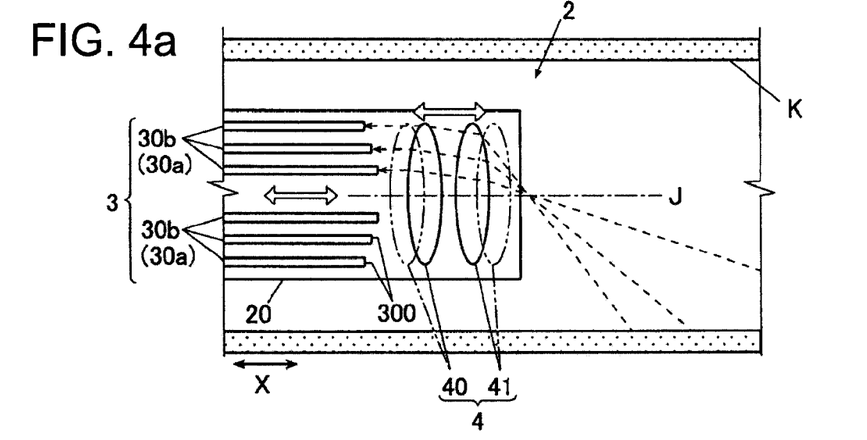
FIG. 4 is a conceptual view showing a schematic constitution of an optical probe in the second embodiment.

The optical probe 2 concerning the 2nd embodiment is also inserted in lumen K in the living body along the direction of an axis X, and has the objective optical system 4 and optical fiber group 3 in the tubular sheath 20 as shown in FIG. 4*a*. In addition, detailed explanation is omitted by giving a same sign to below about the same function member as FIG. 2 and FIG. 3.

The objective optical system 4 has two plus lenses 40, 41 which have plus refractive power. These plus lenses 40 and 41 are arranged towards the tip side of the optical probe 2 in the state where it countered mutually, and are coinciding the optical axis J with the central axis of the optical probe 2 respectively, in this embodiment. In addition, as such an objective optical system 4, a zoom lens well known from the former can be used.

In addition, although explained as having the two plus lenses 40, 41 as the objective optical system 4, it is not limited to this, has three or more lenses, or is good also as a negative lens being included.

A plurality of optical fiber 30*b* is arranged by the position which directed toward the tip surface 300 to the objective optical system 4, and is offset from the optical axis J of the objective optical system 4, and receives the fluorescence passing the objective optical system 4 from the tip surface 300.

Moreover, as a desirable embodiment, a plurality of the tip surface 300 is arranged in the shape of a concentric circular about the optical axis J of the objective optical system 4, and the mutual position of the tip surface 300 is shifted along the optical axis J (the direction of an axis X of the optical probe 2) of the objective optical system 4 according to the amount of offset from the optical axis J of the objective optical system 4.

Furthermore, as a more desirable embodiment, when the tip surface 300 of a plurality of optical fiber 30*b* for receiving light is arranged closer the tip side of the optical probe 2, the tip surface 300 is close to the optical axis J of the objective optical system 4. However, the tip surface 300 is arranged by the other embodiment as long as the position of the tip side of the optical fiber 30*b* of which amounts of offset from the optical axis J of the objective optical system 4 differ mutually at least among the plurality of optical fiber 30*b*.

Figure 4B:
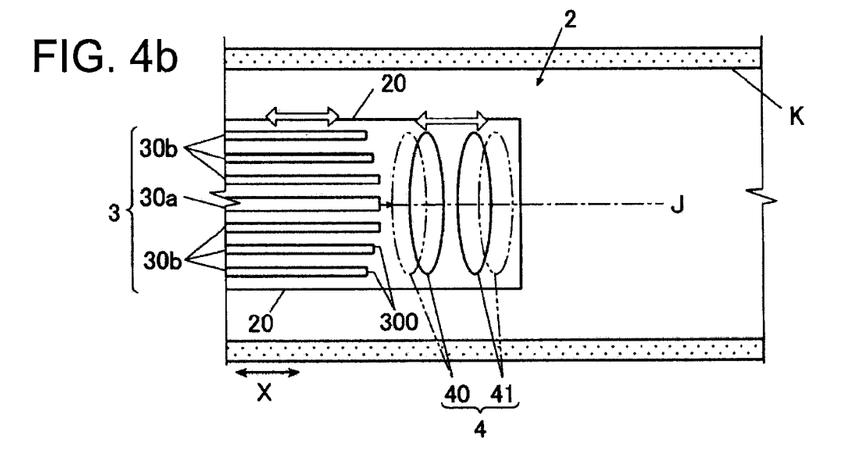
Figure 4C:
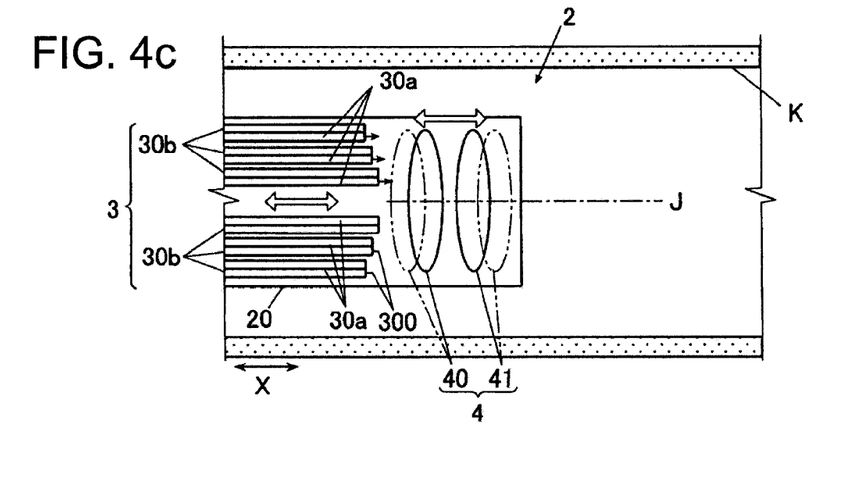

Moreover, the optical fiber group 3 has optical fibers 30*a* for irradiating the excitation light which is generated by the light source 10 and irradiated as an emission light, parallel light or convergence light to the observation object part of physiological tissue through the objective optical system 4 like the 1st embodiment. This optical fiber 30*a* is sufficient the same as that of optical fiber 30*b* for receiving light as shown in FIG. 4*a*, it is sufficient the separate as shown in FIGS. 4*b* and 4*c*. In addition, in FIG. 4*b*, the only one optical fiber 30*a* is formed on the optical axis J of the objective optical system 4, and a plurality of optical fiber 30*a* is arranged side by side to each optical fiber 30*b* in FIG. 4*c*. However, the optical fiber 30*a* of FIG. 4*c* irradiates an excitation light (convergence light) which amount of the diffusion degree is small only to the observation object part through the objective optical system 4, in contrast, the optical fiber 30*a* of FIG. 4*b* irradiates the excitation light (emission light) which amount of the diffusion degree is larger than the optical fiber 30*a* of FIG. 4*c* through the objective optical system 4 since it is necessary to irradiate the excitation light with the observation object part corresponding to each optical fiber 30*b*.

In addition, as for the above optical fiber 30*a* and 30*b* is desirable to consist of bundle fibers.

Moreover, as shown in FIG. 1, the optical probe 2 is provided with the moving mechanism section 25 which moves at least two of the plus lens 40, 41 and optical fiber group 3 along the optical axis J of the objective optical system 4 independently, this moving mechanism section 25 is connected with controller 21 for an operator to operate. This moving mechanism section 25 optimizes the intensity of the fluorescence received by the optical fiber 30*b* (convergence degree by the objective optical system 4) and the position of the observation object part by moving (refer to the allow in FIG. 4) the at least two of the plus lens 40, 41 and optical fiber group 3 along the optical axis J. Moreover, the plus lens 40, 41 and optical fiber group 3 are desirable to move in the sealed space in the optical probe 2. Moreover, as the above moving mechanism section 25, well-known mechanisms, such as a cam mechanism or a mechanism using a plurality of a voice coil motor, is applied, for example.

Since the optical probe 2 of the 2nd embodiment is provided with the objective optical system 4 which has two plus lens 40, 41 which are arranged towards the tip side of the optical probe 2 in the state which countered mutually, a plurality of optical fiber 30*b* which tip surface 300 is arranged towards the objective optical system 4 and in a position offset from an optical axis J of the objective optical system 4 and receives the fluorescence passing the objective optical system 4 from the tip surface 300, and the moving mechanism section 25 which moves at least two of a optical fiber 30*b* and plus lens 40, 41 along the optical axis J of the objective optical system 4, as a dashed line and allow shows in FIG. 4*a*, so the optical probe 2 changes the degree of converging (image formation) and focal length of the objective optical system 4, and converges the fluorescence from the wall surface of the optical probe 2 side to the tip surface 300 of each optical fiber 30b. Therefore, when the optical probe 2 is inserted in lumen K, the fluorescence from the wall surface located in the side of the optical probe is certainly receivable.

Since a plurality of the optical fiber 30b is provided same as the optical probe 2 of the 1st embodiment, fluorescence from a plurality of the observation object part is detectable, respectively. Therefore, diagnostic velocity is accelerable.

And since the position of the tip surface 300 of the optical fiber 30b where the amounts of offset from the optical axis J of the objective optical system 4 differ mutually at least among a plurality of optical fiber is mutually shifted along the optical axis J of the objective optical system 4, the fluorescence from the wall surface of the probe side in each different position along the optical axis J of the objective optical system 4 is converged (image formation) to the tip surface 300 of each optical fiber 30b. Therefore, the fluorescence from the wall surface of the side of the optical probe is certainly receivable. Moreover, fluorescence can be detected from plural part, without moving the main part portion of the optical probe 2 in the direction of optical axis J of the objective optical system 4.

Moreover, when the tip surface 300 of a plurality of optical fiber 30b is arranged closer the tip side of the optical probe 2, the tip surface 300 is close to the optical axis J of the objective optical system 4, the fluorescence from the wall surface of the optical probe 2 side is certainly converged (image formation) to the tip surface 300 of each optical fiber 30b by the objective optical system 4. Therefore, the fluorescence from the surface of a wall located in the probe side is more certainly receivable.

Tip surface 300 of a plurality of optical fiber 30b is arranged in the shape of a concentric circular about the optical axis J of the objective optical system 4, the fluorescence is detectable from the annular observation object part.

Figure 5A:
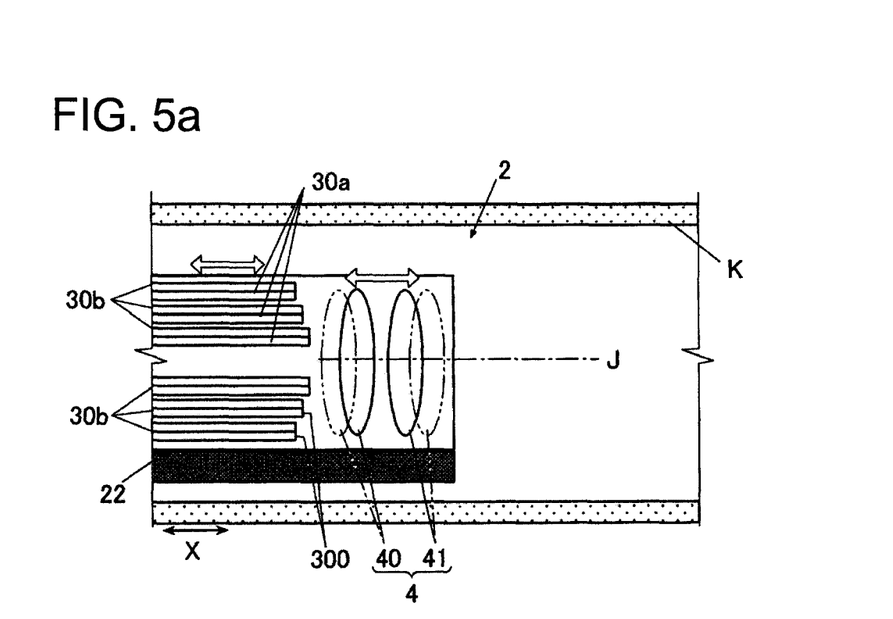
FIG. 5 is a conceptual view showing a schematic constitution of an optical probe in the second embodiment.
Figure 5B:
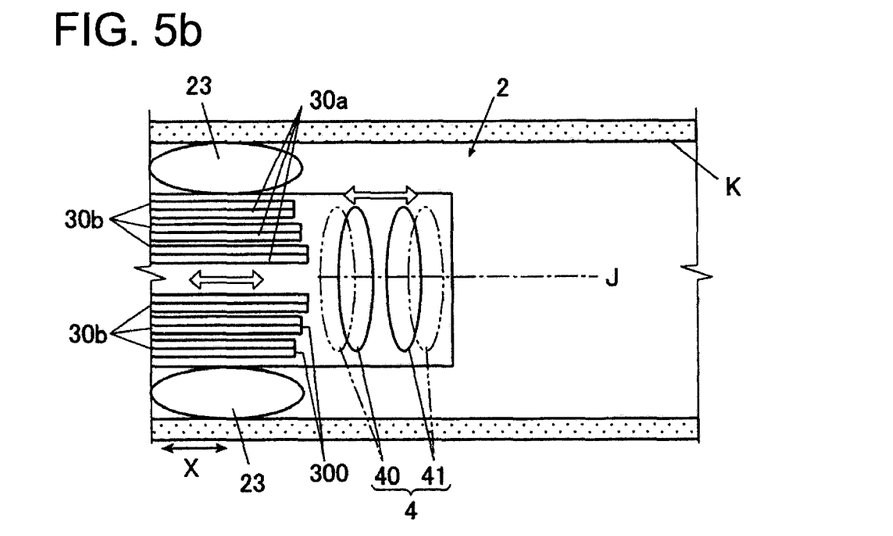

Moreover, it is good as composition of FIG. 5a and FIG. 5b as well as FIG. 3a and FIG. 3b, so the state in lumen K is sighted. Moreover, in FIG. 5a, the optical probe 2 is provided a camera 22 which takes a photograph along the direction of an axis X, in this case, the state in lumen K can be sighted.

Moreover, in FIG. 5b, the optical probe 2 is provided a balloon 23 which inflates in the diameter direction (the rectangular direction to the direction of an axis X) and sticks to the inner wall of lumen K, so the observation object part can be prevented from shifting during observation.

DESCRIPTION OF REFERENCE NUMERALS 1 diagnostic apparatus
2 optical probe
4 objective optical system (plus lens)
40, 41 plus lens (lens)
3 optical fiber group (a plurality of a optical fiber)
23 balloon
25 moving mechanism section
30b optical fiber for receiving light
300 tip surface of an optical fiber
J optical axis of objective optical system (optical axis of plus lens)
K lumen

What is claimed is:

1. A probe, which is inserted into a lumen of inside of a body, irradiates an observation object part of a physiological tissue with excitation light, and detects fluorescence resulting from the excitation light, wherein the probe comprising:
a plus lens arranged facing toward a tip side of the probe;
a plurality of optical fibers,
wherein tip surfaces of the plurality of optical fibers are directed toward the plus lens,
wherein the plurality of optical fibers are arranged in positions offset from an optical axis of the plus lens,
wherein the plurality of optical fibers comprise an optical fiber for irradiating the excitation light and a plurality of optical fibers for receiving the fluorescence at the tip surfaces through the plus lens,
wherein the tip surface of the optical fibers are directed toward the optical axis of the plus lens,
wherein when the tip surfaces of the plurality of optical fibers are arranged closer the tip side of the probe, the tip surfaces are closer to the optical axis of the plus lens,
wherein positions of the tip surface of at least optical fibers of which an amount of offset from the optical axis of the plus lens differ mutually among the plurality of optical fibers for receiving the fluorescence are shifted mutually along the optical axis of the plus lens, and
a light source to supply the excitation light to the optical fiber for irradiating the excitation light and a spectroscope to measure intensity of some wavelength from the detected fluorescence by the plurality of optical fibers for receiving the fluorescence.

2. The probe of claim 1, wherein the tip surfaces of the plurality of optical fibers are arranged in a shape of a concentric circular about the optical axis of the plus lens.

3. The probe of claim 1, further comprising a moving mechanism section moving at least one of the plus lens and the plurality of optical fibers along optical axis of the plus lens.

4. The probe of claim 1, further comprising a balloon inflating in a diameter direction of the probe at a peripheral part to be stuck to the inner wall of lumen.

* * * * *